United States Patent
Dobrovolny

[11] Patent Number: 5,899,627
[45] Date of Patent: May 4, 1999

[54] CLAMP FOR RETRACTOR SUPPORT

[75] Inventor: Walter J. Dobrovolny, St. Paul, Minn.

[73] Assignee: Minnesota Scientific, Inc., Minneapolis, Minn.

[21] Appl. No.: 08/710,164

[22] Filed: Sep. 12, 1996

[51] Int. Cl.⁶ .................................................. A61B 17/02
[52] U.S. Cl. ........................ 403/391; 403/385; 403/384; 403/DIG. 9
[58] Field of Search .................................. 403/385, 389, 403/384, 391, DIG. 9, 90; 600/228, 230, 231, 233, 234; 24/535

[56] References Cited

U.S. PATENT DOCUMENTS

| | | | |
|---|---|---|---|
| 1,710,377 | 4/1929 | Niflot | 600/230 X |
| 2,697,433 | 12/1954 | Zehnder . | |
| 3,046,072 | 7/1962 | Douglass, Jr. et al. | 600/230 X |
| 3,211,405 | 10/1965 | Fey et al. | 248/183 |
| 3,221,743 | 12/1965 | Thompson et al. | 600/234 X |
| 3,539,208 | 11/1970 | Gonsalves . | |
| 3,572,326 | 3/1971 | Jensen | 600/234 X |
| 3,783,547 | 1/1974 | Bystrom et al. | 43/21.2 |
| 4,099,521 | 7/1978 | Nestor et al. | 600/228 |
| 4,708,510 | 11/1987 | McConnell et al. | 403/90 |
| 4,767,231 | 8/1988 | Wallis | 403/56 |
| 4,809,694 | 3/1989 | Ferrara | 128/303 B |
| 4,917,527 | 4/1990 | Bollinger | 403/90 |
| 4,949,707 | 8/1990 | LeVahn et al. | 128/20 |
| 4,955,891 | 9/1990 | Carol | 606/130 |
| 4,971,037 | 11/1990 | Pelta | 600/234 |
| 4,974,802 | 12/1990 | Hendren | 248/181 |
| 5,020,195 | 6/1991 | LeVahn | 24/514 |
| 5,242,240 | 9/1993 | Gorham | 403/391 |
| 5,249,766 | 10/1993 | Vogt | 248/181 |
| 5,263,956 | 11/1993 | Nobles | 606/130 |

Primary Examiner—Anthony Knight
Attorney, Agent, or Firm—Kinney & Lange, P.A.

[57] ABSTRACT

A retractor support apparatus of the present invention includes a first support arm, a second support arm, and a first clamping member. The first and second support arms are each attached to a pivot ball. The first clamping member has a clamping bore that is adapted to receive and engage the pivot balls. The first clamping member retains the first and second support arms in a selected position when the clamp is in an open position. The first clamping member secures the first and second support arms in the selected position when the clamp is in clamping position.

10 Claims, 4 Drawing Sheets

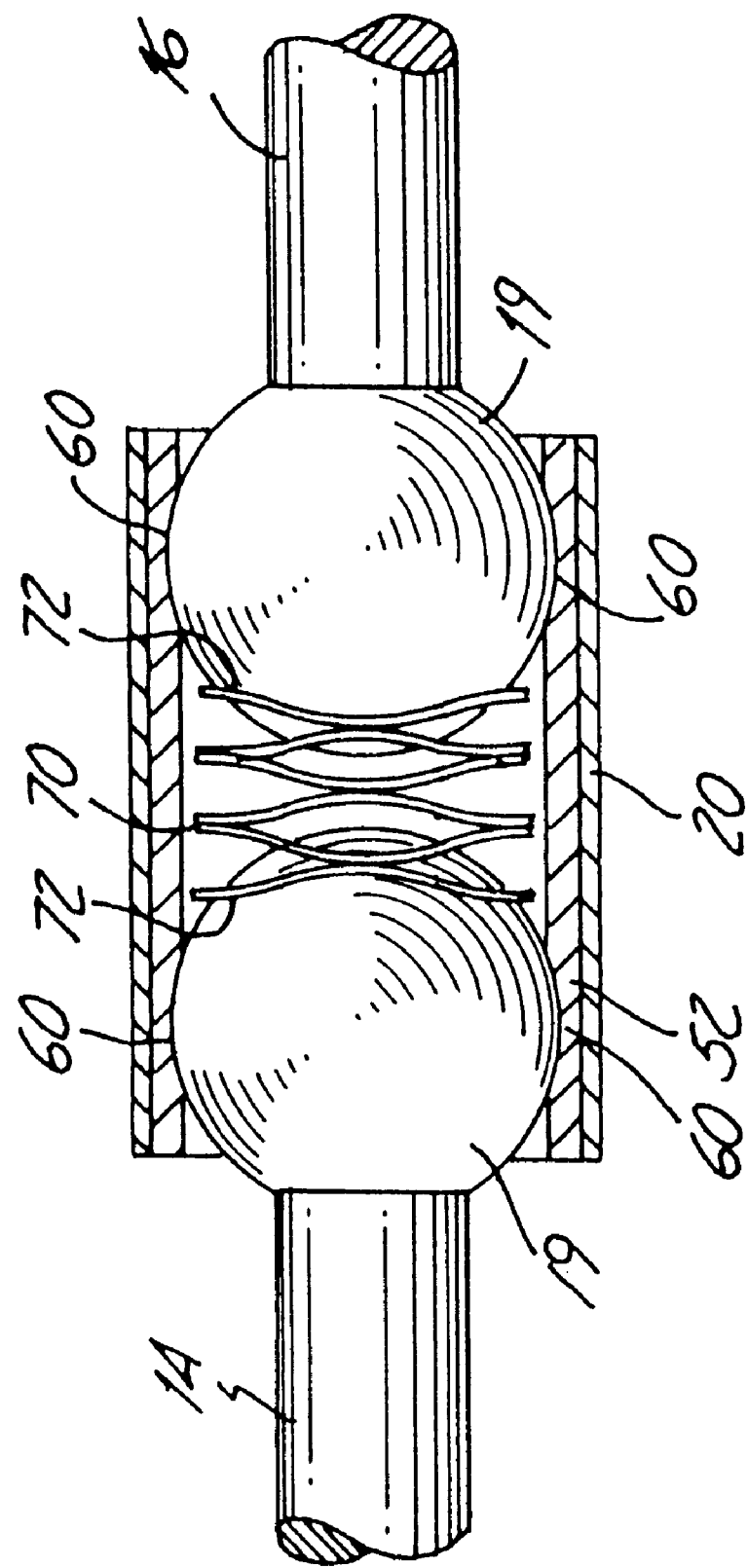

CLAMP FOR RETRACTOR SUPPORT

BACKGROUND OF THE INVENTION

The present invention relates generally to a surgical retractor apparatus. More particularly, the present invention relates to a clamp for use with a retractor support apparatus having a plurality of retractor support arms.

While performing certain surgical techniques, it is desirable to retract tissue adjacent an incision to enhance a surgeon's ability to perform the desired surgical technique. This is typically accomplished by mounting a retractor apparatus to an operating table. One such prior art retractor apparatus is disclosed in LeVahn et al. U.S. Pat. No. 4,949,707, which is assigned to the assignee of the present application.

The LeVahn et al. retractor apparatus includes an extension rod that is attached to a first support rod with a first clamp. The LeVahn et al. retractor apparatus also includes a second support rod that is attached to the first support rod with a second clamp. The first and second support rods are configured to extend over the surgical table on opposite sides of the incision.

When using the LeVahn et al. retractor apparatus, the extension rod is mounted with respect to the operating table using a mounting bracket such as is disclosed in LeVahn et al. The first support rod is oriented in a desired position and the first clamp is moved to a closed position. Next, the second support rod is oriented in a desired position and the second clamp is moved to a closed position. At this point, it is possible to attach retractors to the retractor support.

The clamps used in conjunction with the prior art retractor apparatuses take a variety of configurations. Two such clamps that have been used with prior art retractor apparatus are disclosed in LeVahn, U.S. Pat. No. 5,020,195, and Gorham, U.S. Pat. No. 5,242,240, both of which are assigned to the assignee of the present application. The LeVahn and Gorham clamps each contain a first clamp member and a second clamp member, which is pivotally mounted to the first clamp member. The first and second clamp members are each adapted to receive a retractor support arm.

The LeVahn and Gorham clamps also include a handle for moving the clamp from an open position to a clamping position. When the clamp is in the open position, the first clamp member may be pivoted with respect to the second clamp member. When the clamp is in the clamping position, the first clamp member is maintained in a fixed relationship with respect to the second clamp member.

SUMMARY OF THE INVENTION

The present invention is a retractor support apparatus that includes a first support arm, a second support arm, and a first clamping member. The first support arm is fixedly attached to a first pivot ball and the second support arm is fixedly attached to a second pivot ball.

The first clamp member includes a clamping bore that is adapted to receive and engage the first and second pivot balls. The first clamping member retains the first and second support arms in a selected position when the first clamping member is in an open position. The first clamping member secures the first and second support arms in the selected position when the first clamping member is in a clamping position.

BRIEF DESCRIPTION OF THE DRAWINGS

FIG. 4 is a sectional view of the ball joint clamp, which is taken along a line 4—4 in FIG. 1.

DETAILED DESCRIPTION OF THE PREFERRED EMBODIMENTS

Figure 1:
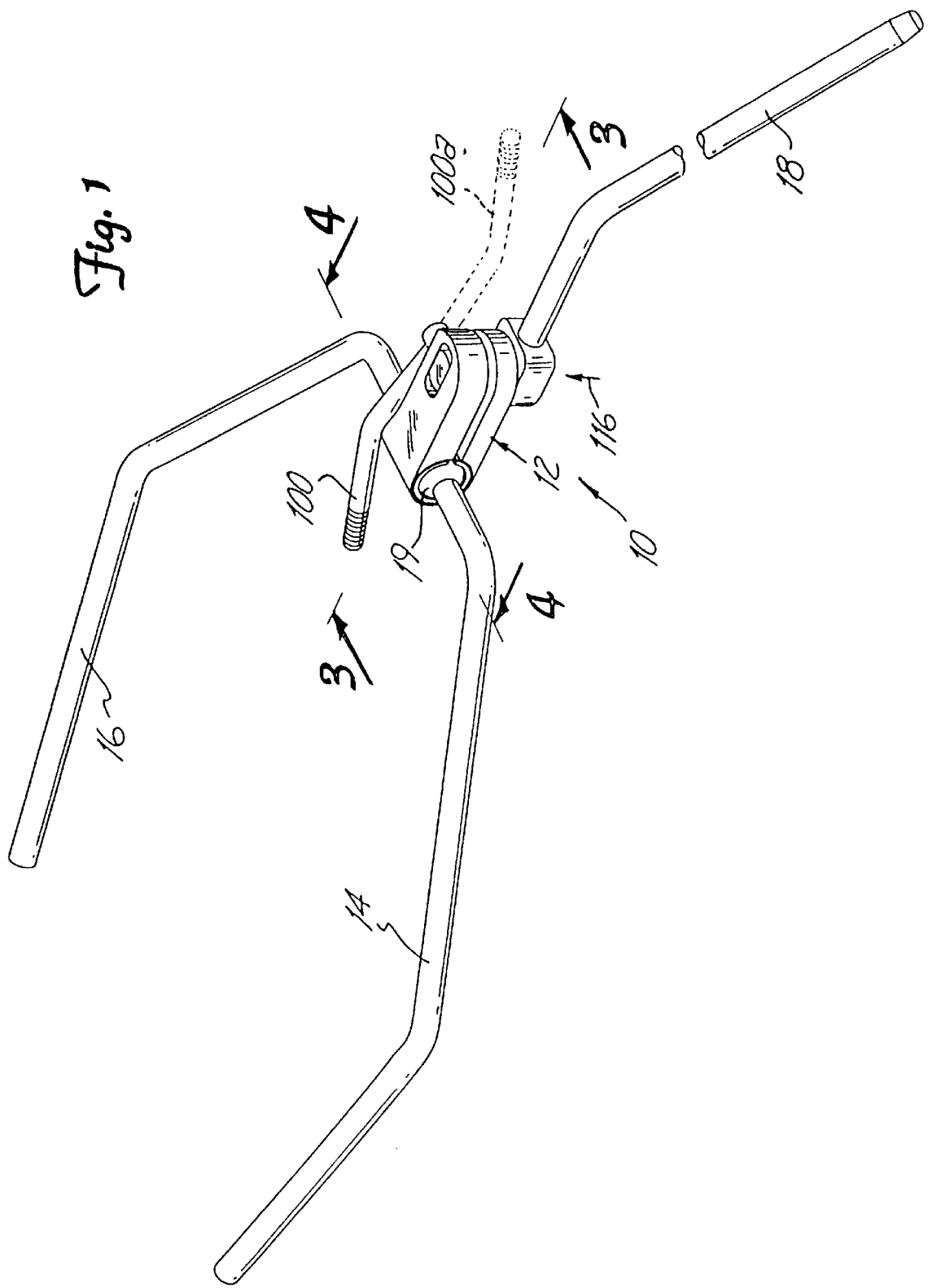
FIG. 1 is a perspective view of a ball joint clamp of the present invention.

A retractor support apparatus according to the present invention is most clearly illustrated at 10 in FIG. 1. The retractor support apparatus 10 is particularly suited for use with mounting surgical instruments, such as retractors, with respect to an operating table (not shown). The retractor support apparatus 10 includes a clamp 12, a first support arm 14, a second support arm 16, and an extension rod 18. The first and second support arms 14, 16 each have a pivot ball 19 attached thereto.

An advantage of the retractor support apparatus 10 of the present invention is that when the clamp 12 is in an open position, the clamp 12 allows the first and second support arms 14, 16 to be moved to a selected position and then retains the first and second support arms 14, 16 in the selected position. Therefore, a surgeon may move the first and second support arms to the selected position without needing to hold the support arms until the arms are clamped. As used herein, the term "retains" means that the first and second support arms 14, 16 remain in the selected position once the first and second support arms 14, 16 are placed in the selected position without need of additional or other support.

When the clamp 12 is in a clamping position, the clamp 12 secures the first and second support arms 14, 16 in the selected position. As used herein, the term "secures" means that the first and second support arms 14, 16 remain in the selected position even when forces are placed upon the first and second support arms 14, 16.

Retaining the first and second support arms 14, 16 in the selected position when the clamp 12 is in the open position enhances the ability to position the retractor support apparatus 10 of the present invention because the first and second support arms 14, 16 do not need to be held in the selected position when the clamp 12 is in the open position.

The clamp 12 includes a first clamping member 20 and a second clamping member 22. The first clamping member 20 is preferably constructed from a block of stainless steel that is machined to form an upper clamp leg 24 and a lower clamp leg 26, as most clearly illustrated in FIG. 2. A slot 28 separates the upper clamp leg 24 and the lower clamp 26. Proximate to a first end 30 of the first clamping member 20, the first clamping member 20 includes a clamping bore 32, which is in communication with the slot 28.

The first clamping member 20 is constructed to allow the upper clamp leg 24 and the lower clamp leg 26 to move towards each other. Moving the upper clamp leg 24 and the lower clamp leg 26 towards each other decreases the circumference of the clamping bore 32 thereby enables pivot balls 19 to be clamped within the clamping bore 32.

Proximate to a second end 34 of the first clamping member 20, the first clamping member 20 has a bolt bore 40 formed therein. The bolt bore 40 is preferably orientated substantially transverse to the clamping bore 32. The upper clamp leg 24 additionally has a handle bore 42 formed therein. The handle bore 42 preferably has a substantially cylindrical shape and is in communication with the bolt bore 40.

The clamping bore 32 is adapted to receive a sleeve 52. The sleeve 52 has a slot 54 removed therefrom. The slot 54 allows the sleeve 52 to constrict in response to a force applied to an outer surface 56 of the sleeve 52 such as when the upper and lower clamp legs 24, 26 are moved towards each other.

Proximate to each end 58 of the sleeve 52, the sleeve includes a semi-circular channel 60 that extends around an inner surface 62 of the sleeve 52. The channels 60 are each shaped to conform with an outer surface of the pivot balls 19 to increase the surface area over which the sleeve 52 engages the pivot balls 19. The increased surface area provided by the channels 60 not only enhances the ability of the clamp 12 to secure the support arms 14, 16 in the selected position when the clamp 12 is in the clamping position but the increased surface area contact between the sleeve 52 and the pivot balls 19 also assists to retain the support arms 14, 16 in the selected position when the clamp 12 is in the open position.

The clamp 12 also preferably includes a spring 70, which is positioned in the sleeve 52 so that opposite ends 72 of the spring 70 engage the pivot balls 19, as most clearly illustrated in FIG. 4. The spring 70 is selected with sufficient resiliency so that the spring 70 biases the pivot balls 19 apart from each other and into the inner surface 62 of the sleeve 52. The spring 70 thereby retains the pivot balls 19 in a selected position with respect to the sleeve 52 when the clamp 12 is in the open position. The spring 70 also permits the pivot balls 19 to be pivoted within the sleeve 52 in response to a force placed on the support arm to which the pivot ball 19 is connected.

The second clamping member 22 has a bolt bore 50 formed therein. The extension rod 18 is preferably fixedly attached to the second clamping member 22. While fixedly attaching the extension rod 18 to the second clamping member 22 reduces the complexity of arranging the retractor support apparatus 10, one of ordinary skill in the art will appreciate that it is also possible to fabricate the second clamping member 22 in other configurations while remaining within the scope of the present invention.

To enhance the ability to retain the first clamping member 20 in a desired position with respect to the second clamping member 22 when the clamp 12 is in the clamping position, a bushing 80 is preferably provided between the first clamping member 20 and the second clamping member 22. The bushing 80 preferably has a frustro-conical upper surface 82 and a frustro-conical lower surface 84.

Figure 3:
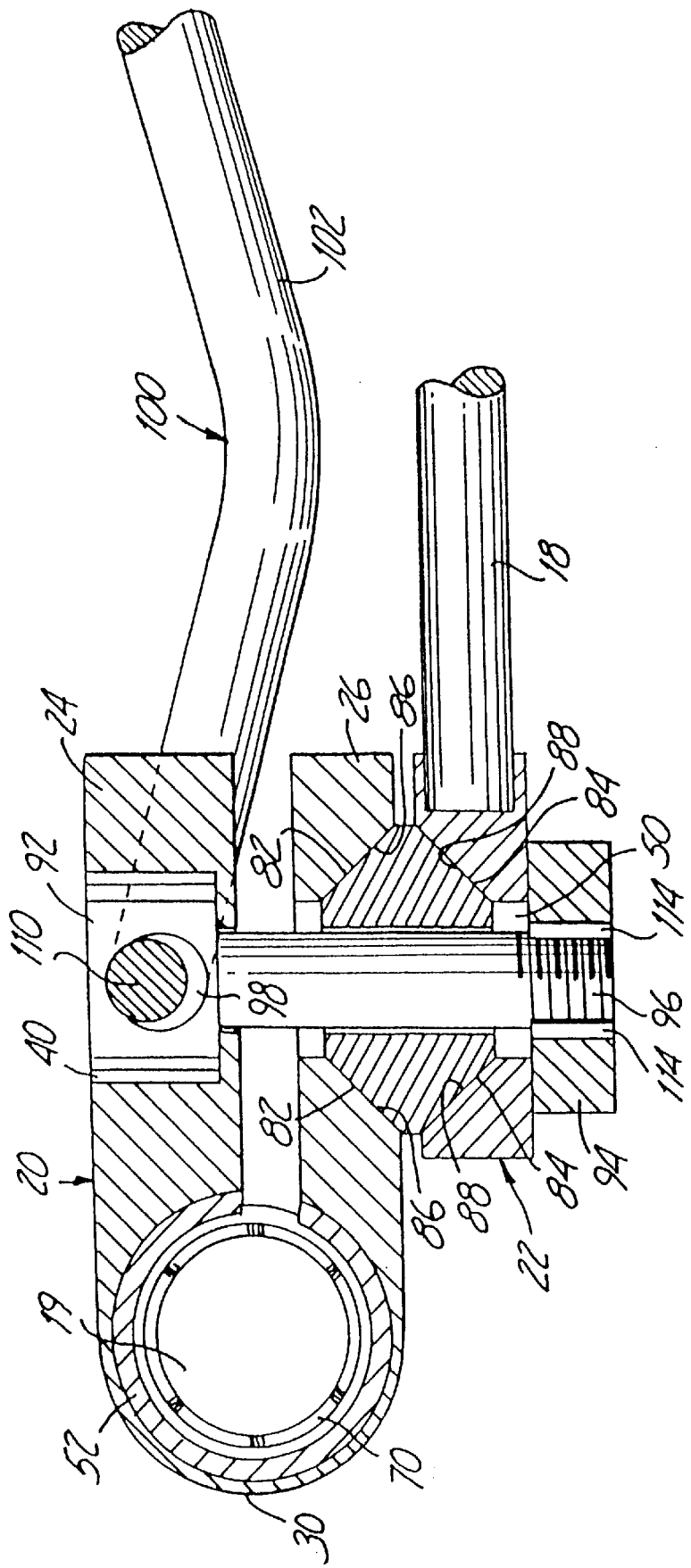
FIG. 3 is a sectional view of the ball joint clamp, which is taken along a line 3—3 in FIG. 1.

When the bushing 80 is formed with frustro-conical upper and lower surfaces 82 and 84, the lower clamp leg 26 preferably includes a frustro-conical lower surface 86 that substantially surrounds the bolt bore 40, as most clearly illustrated in FIG. 3. The frustro-conical lower surface 86 is preferably orientated at substantially the same angle as the frustro-conical upper surface 82 so that the frustro-conical surfaces 82 and 86 are substantially in contact with each other when the bushing 80 is placed adjacent to the first clamping member 20.

Similarly, the second clamping member 22 preferably includes a frustro-conical upper surface 88 that extends around the bolt bore 50. The frustro-conical upper surface 88 is preferably oriented at substantially the same angle as the frustro-conical lower surface 84 so that the frustro-conical surface 84 and 88 are substantially in contact with each other when the bushing 80 is placed adjacent to the second clamping member 22.

To maintain the first clamping member 20 and the second clamping member 22 in an assembled configuration while allowing the clamp 12 to be moved between the open and clamping positions, the clamp 10 includes a fastening mechanism 90. The fastening mechanism 90 preferably includes a bolt 92 and a nut 94. The nut 94 engages a threaded region 96 on the bolt 92. Opposite the threaded region 96, the bolt 92 includes a handle bore 98 extending therethrough.

The clamp 12 is moved between the open and clamping positions with a clamp handle 100. The clamp handle 100 preferably moves the clamp 12 between the open and clamping positions using a camming action. The clamp handle 100 includes a grip portion 102 and a pivot portion 104, which is preferably oriented substantially perpendicular to the grip portion 102. The pivot portion 104 preferably has a substantially cylindrical outer surface 106 that allows the pivot portion 104 to rotate within the handle bore 42.

The camming action is provided by an eccentric section 108 on the pivot portion 104. The eccentric section 108 is preferably located at an intermediate location on the pivot portion 104, as most clearly illustrated in FIG. 2. The eccentric portion 108 is offset from a central axis 110 of the pivot portion 104, as most clearly illustrated in FIG. 3. This configuration allows the eccentric portion 108 to engage the clamp handle 100 through the handle bore 98.

Figure 2:
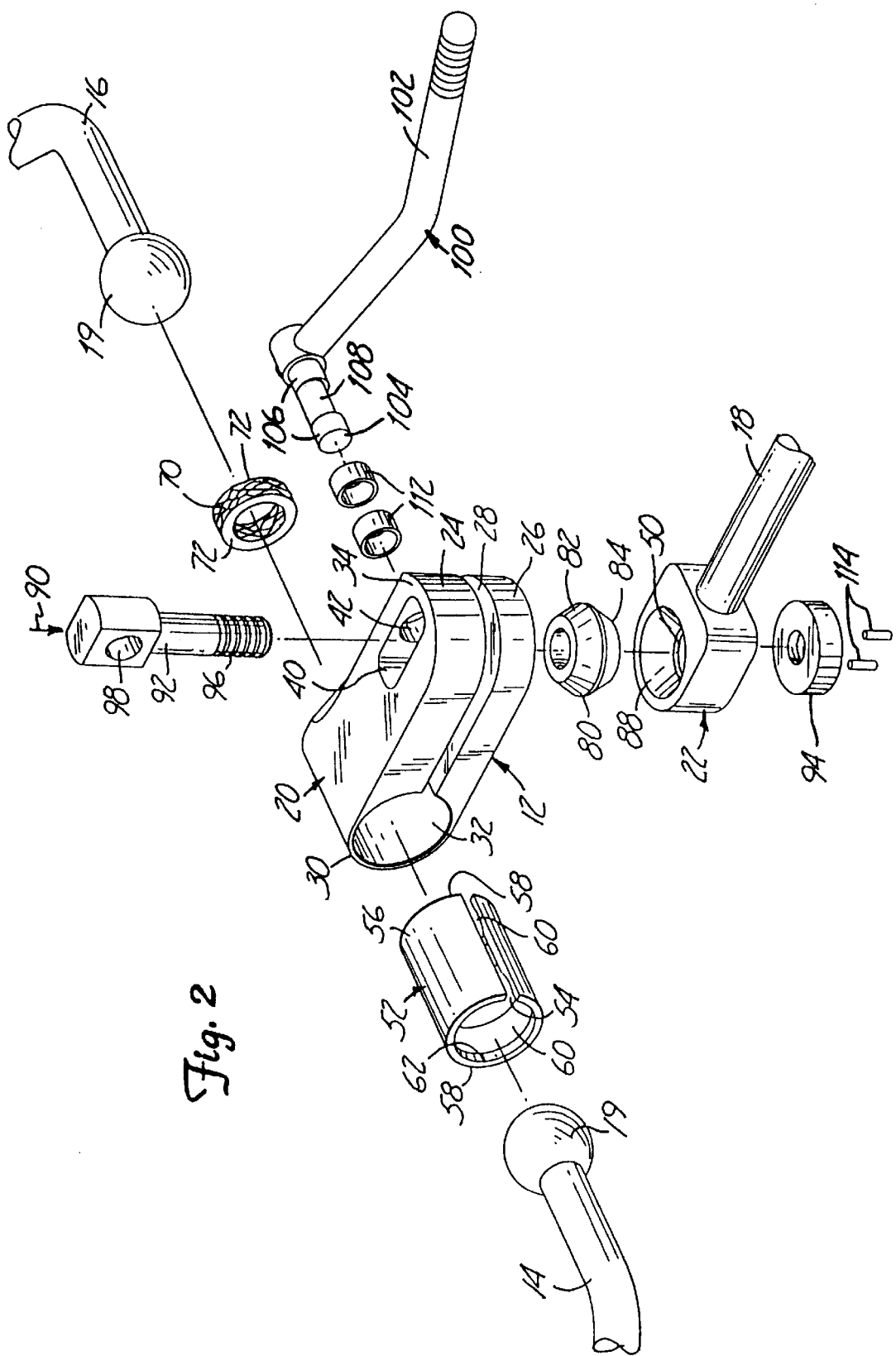
FIG. 2 is an exploded perspective view of the ball joint clamp.

To further enhance the operation of the clamp 12, the clamp 12 preferably includes a pair of sleeve bearings 112, as most clearly illustrated in FIG. 2. The sleeve bearings 112 are placed over the outer surface 106 on either side of the eccentric section 108. The sleeve bearings 112 are preferably constructed from a strong and durable plastic such as Victrex PEEK, a linear aromatic polymer of poly(alyletherketone). Victrex PEEK is described in UK Patent No. 432 02 24 and may be obtained from ICI of Great Britain.

The retractor support apparatus 10 is assembled by inserting the bolt 92 through the bolt bore 40 so that the handle bore 98 is adjacent to the handle aperture 42. The pivot portion 104 is then inserted through the handle aperture 42 until the eccentric section 108 is adjacent to the handle bore 98. The nut 94 is then screwed onto the threaded region 96 of the bolt 92.

To preclude the clamp 12 from being disassembled by removing the nut 94 from the bolt 92, retaining pins 114 are driven between the nut 94 and the bolt 92. The retaining pins 114 deform the threads on both the nut 94 and the bolt 92 and thereby preclude the nut 94 from being removed from the bolt 92.

In operation, the clamp 12 is initially in an open position, as most clearly illustrated in FIG. 1. When the clamp 12 is in the open position, the clamp 12 permits the first and second support arms 14, 16 to be moved to a selected position. Once the first and second support arms 14, 16 are in the selected position, the clamp 12 retains the first and second support arms 14, 16 in the selected position. It is also possible to rotate the first clamping member 20 with respect to the second clamping member 22 when the clamp 12 is in the open position.

The clamp 12 is then moved to the clamping position by rotating the clamp handle 100 with respect to the first clamping member 20, as indicated by arrow 116 in FIG. 1 until the clamp handle 100 is in the position indicated by broken lines 100a. Rotation of the clamp handle 100 causes the eccentric section 108 to urge the bolt 92 towards the upper clamp leg 24, as indicated by arrow 116. Movement of the bolt 92 towards the upper clamp leg 24 pulls the second clamping member 22 towards the upper clamp leg 24, which thereby causes the lower clamp leg 26 to be urged towards the upper clamp leg 24. The first clamping member 20 is thereby retained in a fixed relationship with respect to the second clamping member 22.

Movement of the lower clamp leg 26 towards the upper clamp leg 24 decreases the circumference of the clamping bore 32, which causes the sleeve 52 to constrict over the pivot balls 19. Constriction of the sleeve 52 over the pivot balls 19 secures the first and second support arms 14, 16 in the selected position with respect to the clamp 12.

Although the present invention has been described with reference to preferred embodiments, workers skilled in the art will recognize that changes may be made in form and detail without departing from the spirit and scope of the invention.

What is claimed is:

1. A retractor support apparatus comprising:

a first support arm;

a second support arm, wherein the first and second support arms each have a pivot ball attached thereto;

a first clamping member having a clamping bore adapted to receive and engage the pivot balls, wherein the first clamping member retains the first and second support arms in a selected position when the clamp is in an open position, and wherein the first clamping member secures the first and second support arms in the selected position when the clamp is in a clamping position; and a sleeve positioned in the clamping bore wherein the sleeve is constrictable in response to the clamping member being in the clamped position to retain the support arms in the selected position.

2. The retractor support apparatus of claim 1, and further comprising a second clamping member pivotally mounted with respect to the first clamping member.

3. The retractor support apparatus of claim 2, and further comprising:

a bolt retained in relation to the second clamping member; and a clamp handle that operably engages the bolt and the first clamping member for moving the clamp between the open and clamping positions.

4. The retractor support apparatus of claim 3, wherein clamp handle includes an eccentric section, and wherein the clamp handle engages the bolt through the eccentric section.

5. The retractor support apparatus of claim 1, and further comprising a spring positioned between the pivot balls inside of the sleeve.

6. A retractor support apparatus comprising:

a first support arm;

a second support arm, wherein the first and second support arms each have a pivot ball attached thereto;

an extension rod;

a clamp comprising:

a first clamping member having a clamping bore formed therein, wherein the clamping bore is adapted to receive and engage the pivot balls;

a second clamping member pivotally mounted to the first clamping member, wherein the extension rod is attached to the second clamping member; and a handle operably engaging the first and second clamping members for moving the clamp between an open position and a clamping position; and a sleeve positioned in the clamping bore wherein the sleeve is constrictable in response to the clamping member being in the clamped position to retain the support arms in the selected position.

7. The retractor support apparatus of claim 6, wherein the first clamping member retains the first and second support arms in a selected position when the clamp is in an open position, and wherein the first clamping member secures the first and second support arms in the selected position when the clamp is in a clamping position.

8. The retractor support apparatus of claim 6, and further comprising:

a bolt retained in relation to the second clamping member, wherein the handle engages the bolt and the first clamping member for moving the clamp between the open and clamping positions.

9. The retractor support apparatus of claim 8, and further comprising a spring positioned between the pivot balls inside of the sleeve.

10. A clamp for use in a retractor support apparatus, the clamp retaining first and second support arms in a selected position, the clamp comprising:

pivot balls attached to the first and second support arms; and a first clamping member having a clamping bore adapted to receive and engage the pivot balls such that when the first clamping member is in a clamping position, wherein the first clamping member retains the pivot balls in a selected position when the clamp is in an open position, and wherein the first clamping member secures the pivot balls in the selected position when the clamp is in a clamping position;

a sleeve positioned in the clamping bore wherein the first clamping member provides a force that constricts the sleeve to retain the pivot balls in the select position thereby placing the clamping member in the clamping position;

a spring positioned between the pivot balls inside of the sleeve;

a second clamping member pivotally mounted with respect to the first clamping member;

a bolt retained in relation to the second clamping member; and a clamp handle that operably engages the bolt and the first clamping member for moving the clamp between the open and clamping positions.

* * * * *